United States Patent
Farnham et al.

(10) Patent No.: US 7,220,844 B2
(45) Date of Patent: May 22, 2007

(54) LIVER TUMOR MARKER SEQUENCES

(75) Inventors: Peggy J. Farnham, Madison, WI (US); Carrie R. Graveel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 530 days.

(21) Appl. No.: 10/017,410

(22) Filed: Dec. 14, 2001

(65) Prior Publication Data
US 2002/0115094 A1    Aug. 22, 2002

Related U.S. Application Data

(60) Provisional application No. 60/255,674, filed on Dec. 14, 2000.

(51) Int. Cl.
*C12N 15/11* (2006.01)

(52) U.S. Cl. .......................... 536/23.1; 435/6; 435/7.1; 435/320.1; 435/325

(58) Field of Classification Search ............... 536/23.1, 536/24.31; 435/320.1, 325
See application file for complete search history.

(56) References Cited

U.S. PATENT DOCUMENTS 6,639,063 B1 * 10/2003 Edwards et al. ........... 536/23.5

OTHER PUBLICATIONS

Wu et al., (Apr. 12, 1996, Biochim Biophys Acta. vol. 1315, issue No. 3, pp. 169-175).*
Bonaldo et al., (1996, Genome Research, vol. 6, pp. 791-806).*
Alberts et al. (Molecular Biology of the Cell, 3rd edition, 1994, p. 465).*
Shantz and Pegg (Int J of Biochem and Cell Biol., 1999, vol. 31, pp. 107-122).*
McClean and Hill (Eur J of Cancer, 1993, vol. 29A, pp. 2243-2248).*
Fu et al (EMBO Journal, 1996, vol. 15, pp. 4392-4401).*
Greenbaum et al. (Genome Biology, 2003, vol. 4, Issue 9, pp. 117.1-117.8).*
Bussenmakers et al., Cancer Res. Dec. 1, 1999;59 :5975-90.*
IDT Oligoanalyzer 3.0 downloaded from world wide web idtdna.com on Feb. 14, 2006.*
Johnson et al., Journal of Neurochemistry, vol. 64 p. 967-8 only Mar. 1995.*
Graveel et al., "Expression profiling and identification of novel genes in hepatocellular carcinomas," *Oncogene* 20:2704-2712 (2001).

* cited by examiner

*Primary Examiner*—Misook Yu
(74) *Attorney, Agent, or Firm*—Quarles & Brady LLP

(57) ABSTRACT

Novel polypeptides and nucleic acids that encode the polypeptides are disclosed. The polypeptides and nucleic acids are differentially expressed in liver tumors relative to expression in normal liver tissues. In humans, the nucleic acid sequence maps to a region of chromosome 9p.

5 Claims, No Drawings

SEQUENCE LISTING

<160> NUMBER OF SEQ ID NOS: 4

<210> SEQ ID NO 1
<211> LENGTH: 4175
<212> TYPE: DNA
<213> ORGANISM: Mus musculus
<220> FEATURE:
<221> NAME/KEY: CDS
<222> LOCATION: (35)..(859)

<400> SEQUENCE: 1

```
ggcacgaggg ctgctccgat gctccagagc ggcc atg ggc gcc ccg cac tgg tgg      55
                                    Met Gly Ala Pro His Trp Trp
                                      1               5 gac cac ctg cgg gct ggc agt tcg gag gtg gat tgg tgc gag gac aac     103
Asp His Leu Arg Ala Gly Ser Ser Glu Val Asp Trp Cys Glu Asp Asn
             10                  15                  20 tac act atc gtg cct gcc att gcc gag ttc tac aac acg atc agc aac     151
Tyr Thr Ile Val Pro Ala Ile Ala Glu Phe Tyr Asn Thr Ile Ser Asn
     25                  30                  35 gtc ttg ttt ttc att tta cct ccc atc tgc atg tgc ttg ttc cgc cag     199
Val Leu Phe Phe Ile Leu Pro Pro Ile Cys Met Cys Leu Phe Arg Gln
 40                  45                  50                  55 tac gca acg tgc ttc aac agc ggc atc tac tta ata tgg acg ctc cta     247
Tyr Ala Thr Cys Phe Asn Ser Gly Ile Tyr Leu Ile Trp Thr Leu Leu
                 60                  65                  70 gtt gta gtg ggg att gga tct gtc tac ttc cat gca acg ctg agt ttc     295
Val Val Val Gly Ile Gly Ser Val Tyr Phe His Ala Thr Leu Ser Phe
             75                  80                  85 ctg ggt cag atg ctt gat gaa ctt gcc att ctg tgg gtt ctg atg tgt     343
Leu Gly Gln Met Leu Asp Glu Leu Ala Ile Leu Trp Val Leu Met Cys
         90                  95                 100 gct ttg gcc atg tgg ttt ccc agg agg tat tta cca aag atc ttt cgg     391
Ala Leu Ala Met Trp Phe Pro Arg Arg Tyr Leu Pro Lys Ile Phe Arg
    105                 110                 115 aat gac agg ggc agg ttc aag gca gtg gtg tgt gtc ctg tct gca att     439
Asn Asp Arg Gly Arg Phe Lys Ala Val Val Cys Val Leu Ser Ala Ile
120                 125                 130                 135 aca acg tgc ttg gcg ttt atc aag ccc gcc atc aac aat att tcc ctg     487
Thr Thr Cys Leu Ala Phe Ile Lys Pro Ala Ile Asn Asn Ile Ser Leu
                140                 145                 150 atg att ctg gga ctt cca tgc act gcg ctg ctt gtt gca gag ctg aag     535
Met Ile Leu Gly Leu Pro Cys Thr Ala Leu Leu Val Ala Glu Leu Lys
            155                 160                 165 agg tgt gac aat gtg cgt gtg ttt aag ctg ggc ctc ttc tct ggc ctc     583
Arg Cys Asp Asn Val Arg Val Phe Lys Leu Gly Leu Phe Ser Gly Leu
        170                 175                 180 tgg tgg act ctg gct ctc ttc tgc tgg atc agc gac caa gcc ttc tgt     631
```

-continued

| | | |
|---|---|---|
| Trp Trp Thr Leu Ala Leu Phe Cys Trp Ile Ser Asp Gln Ala Phe Cys<br>185 190 195 | | |
| gag ctg ctc tcc tcc ttt cac ttc ccc tac ctg cac tgt gtg tgg cat<br>Glu Leu Leu Ser Ser Phe His Phe Pro Tyr Leu His Cys Val Trp His<br>200 205 210 215 | 679 | |
| att ctc atc tgc ctt gct tcg tac ctg ggc tgt gtg tgc ttc gcc tac<br>Ile Leu Ile Cys Leu Ala Ser Tyr Leu Gly Cys Val Cys Phe Ala Tyr<br>220 225 230 | 727 | |
| ttt gat gct gcc tca gag ata cct gag caa ggt cca gtc atc aga ttc<br>Phe Asp Ala Ala Ser Glu Ile Pro Glu Gln Gly Pro Val Ile Arg Phe<br>235 240 245 | 775 | |
| tgg ccc agc gag aaa tgg gct ttt att ggt gtc cct tat gtg tcc ctt<br>Trp Pro Ser Glu Lys Trp Ala Phe Ile Gly Val Pro Tyr Val Ser Leu<br>250 255 260 | 823 | |
| ctg tgt gcc cac aag aag tcg cca gtc aag atc acg tgatggcaag<br>Leu Cys Ala His Lys Lys Ser Pro Val Lys Ile Thr<br>265 270 275 | 869 | |
| gcagtgacca gcttctctac ttacttctat tcgagtgcgc gctgggcttc gtttgctagc | 929 | |
| aaagatggct gaggggggttg aggaattggt gtggtgtggg tgtttaaaat tctgctcctt | 989 | |
| tgtgatctaa ctggaccact gtgcctgacc tccctaggtt aagtagaggg ctcagggaca | 1049 | |
| taaggtgtct tcctcagtat cctttccagg catacgggct tgctgggtta tgtcccataat | 1109 | |
| gacatcaaca gagtagttct ttgggagacc tagggcaacc caaagtttct tgctggagag | 1169 | |
| ggtagcttgc tgtttccacc atttccagac tctcaacccc ctgataaaca agaccttctg | 1229 | |
| atttggtgat gaaaggttcc agaacttttc attttgccgg gagaaactgt ccttcaacaa | 1289 | |
| aaccaagtgg gcaaaacacg tgtgggggt gtgactaaga cgggtggctt gtcactcgca | 1349 | |
| cctcttagct ttcccaggtt ctccacgtgt ttgtggatcc ttccactacc tctgctgaga | 1409 | |
| gatggagcca cggcttcaga gggcaaagct ggcaacaccc tctatgccaa aagctacact | 1469 | |
| cctctttaag cacacattac atagacacta tttctgctct tccagagtgc agcagcctca | 1529 | |
| gacccacaga gaatccttca ggttatgtga agattccaca cacagccccc tcttgtgacc | 1589 | |
| tctgtgagag caaggcctcg ttgtaatcgc ggaggcagct ctggaggctt gactgtggag | 1649 | |
| cgcctgtgaa gattttggaa agcttttctt attggaagct tttggtgtgt cgttacctcc | 1709 | |
| aagattctga ccccgtttct ctgctgtttt taggggatat gtgcttcctg agtgacgtag | 1769 | |
| cctccctagg atgtgggcct ccggcttttg ttttcataat acctggtgct aactggtttc | 1829 | |
| tcagagcact tgctcttct tgatgctggg cggtcactac actctgattg ctggctggg | 1889 | |
| gatcccaggg aggaaggggc agactctgac atgaatgtct ctcacctgca tcctactgtc | 1949 | |
| ttcactgggc tctcttcagg gtatgaagtg ggtatgggt atctcaggga tgtttgtaac | 2009 | |
| tcaggcacct tctgctttct gacattccat tgtcagtggt gagactgcac tcaggggact | 2069 | |
| ggagttggaa caccgttctg agtggtgtcc tgagtctgaa ggagctagct gcgggttctg | 2129 | |
| gcacttctag gatctcttac tctgtttaga accttcacag ggtacaaagt gggaactgga | 2189 | |
| cttaaagagt ttttaaatga atagacttca ttctgctttt gtggctttgg agttttaaaa | 2249 | |
| gtaacttgct gggctatttc ttgtttatag tcacaaatat ttatagaaca tgaaggtgta | 2309 | |
| aaataagttg tcttttatta aattcatagc atttaccaac tctcccaggt agcaaacaca | 2369 | |
| cagtcatttg attggcgatt tacaaggcag gaatacttgg ttttgaatga ttgtatatgt | 2429 | |
| cattttactg tagcttaaaa tatgtttaaa atgactttga gtgaaatgtt tgtggcaacc | 2489 | |
| tagggggttta tggatcagaa ttgcggctga gtcctttggt ttttgagtct agaagttttc | 2549 | |

```
agagggcaaa atcaaactag ccttgtttct ggttcatctt accaggctcg ggagctgccc    2609
ttatatattc tacataagga cttattatac ataagtctgt ataaatgtcc tgaagatgac    2669
acctagctgc cttcatctgg aagggtcgtc tggggctgga gagttggttc aacagttaag    2729
aacccgtgtt gctctctccc agacgaccca gcgacttgtg aggctcataa ccagcaactc    2789
cagccctggg gcatctgacg ccctcttctg acttctaagg gcatttggtg cacacgtaca    2849
tacaggcagg caaacatttt atacatgtaa cgtaataaat gcataagtta gtgagacggc    2909
tgaaggaaag gagttttaga tgcaaggttt agtctgacct gagtgccctt ccttagccgc    2969
gatggtgtcc tcaaagtcag ggaagaacca tttcttttt atcaggaaaa ggacttattc     3029
cctagggcct ctgctgacat ccctaggaac agagataaaa tacgatggga tgtgaatgaa    3089
catgcttggg tgaaaggagc cgagtacctg actggaccca gtgggccact ccacaagcg     3149 aagcccggta accgatgtgc actccagaat cttctccctt ctggtagaga tgacatcgat    3209
gagtgatgtc gtgaccactg ggccctgcat gggtgtcggg ctctgttctg ttccgaatct    3269
acctgagatc tcaggacaga ggaagccatg aatgttacca agtggtcatg gctgtcagtg    3329
attttacagt tttgaaccat tattggtttt taggagaatt cttctctctc tagtgccctg    3389
tgatgccaaa gccagcccct cagaagtgtt ccttctgtct gcttccctt gtaatgtgat     3449 ccactcgggg aaatgggtgt ctacccaggg aaaagtgcct accccagtca cgggtcaaca    3509
gtgttgtgtt gaggatcaaa catggctctg tgaaaatact gccacccatt ctattggttg    3569
gatttctcag gagtctgaat cttccctcac gagtcctctt ctcccaaccc ctacccagag    3629
ccaacactgg gatttgaacc ttctctgact ctcttcttcc ctcaggtctg acaactaatg    3689
gtctctgggg acacccagct agggccttcc ccaactcctt atccagctga acttggattc    3749
ttcccaacca gggcttgacc tgggtgctgt tggtcccact ggccaacaac acatctttgg    3809
ccagattggg attctcaata gattttatag acattattct cccacagact ttaaaacatg    3869
gcttgtgtct ttccatacac atccggtcag atttaaaact atttttataac cacaggaatt    3929 aaaccaagca aatagagtac tttcagatat aaactgtgtt tcatacttta tgtagagtgt    3989
gctatgtata ggcggtatgt accctggctg aagtaatatt aaccatagct ctgggaggat    4049
ttacagacct tttgcacttt atgctttttt gtgaactctg ataaccatgg tcaatattaa    4109
agccaataac tggcattttc tgtgaataaa catgcatatg tatctaaaaa aaaaaaaaa    4169 aaaaac                                                              4175
```

<210> SEQ ID NO 2
<211> LENGTH: 275
<212> TYPE: PRT
<213> ORGANISM: Mus musculus

<400> SEQUENCE: 2

```
Met Gly Ala Pro His Trp Trp Asp His Leu Arg Ala Gly Ser Ser Glu
 1               5                   10                  15

Val Asp Trp Cys Glu Asp Asn Tyr Thr Ile Val Pro Ala Ile Ala Glu
            20                  25                  30

Phe Tyr Asn Thr Ile Ser Asn Val Leu Phe Phe Ile Leu Pro Pro Ile
        35                  40                  45

Cys Met Cys Leu Phe Arg Gln Tyr Ala Thr Cys Phe Asn Ser Gly Ile
    50                  55                  60

Tyr Leu Ile Trp Thr Leu Leu Val Val Gly Ile Gly Ser Val Tyr
 65                  70                  75                  80
```

```
Phe His Ala Thr Leu Ser Phe Leu Gly Gln Met Leu Asp Glu Leu Ala
                85                  90                  95

Ile Leu Trp Val Leu Met Cys Ala Leu Ala Met Trp Phe Pro Arg Arg
            100                 105                 110

Tyr Leu Pro Lys Ile Phe Arg Asn Asp Arg Gly Arg Phe Lys Ala Val
        115                 120                 125

Val Cys Val Leu Ser Ala Ile Thr Thr Cys Leu Ala Phe Ile Lys Pro
130                 135                 140

Ala Ile Asn Asn Ile Ser Leu Met Ile Leu Gly Leu Pro Cys Thr Ala
145                 150                 155                 160

Leu Leu Val Ala Glu Leu Lys Arg Cys Asp Asn Val Arg Val Phe Lys
                165                 170                 175

Leu Gly Leu Phe Ser Gly Leu Trp Trp Thr Leu Ala Leu Phe Cys Trp
            180                 185                 190

Ile Ser Asp Gln Ala Phe Cys Glu Leu Leu Ser Ser Phe His Phe Pro
        195                 200                 205

Tyr Leu His Cys Val Trp His Ile Leu Ile Cys Leu Ala Ser Tyr Leu
210                 215                 220

Gly Cys Val Cys Phe Ala Tyr Phe Asp Ala Ala Ser Glu Ile Pro Glu
225                 230                 235                 240

Gln Gly Pro Val Ile Arg Phe Trp Pro Ser Glu Lys Trp Ala Phe Ile
                245                 250                 255

Gly Val Pro Tyr Val Ser Leu Leu Cys Ala His Lys Lys Ser Pro Val
            260                 265                 270

Lys Ile Thr
275

<210> SEQ ID NO 3
<211> LENGTH: 828
<212> TYPE: DNA
<213> ORGANISM: Homo sapiens
<220> FEATURE:
<221> NAME/KEY: CDS
<222> LOCATION: (1)..(825)

<400> SEQUENCE: 3 atg ggc gcc ccg cac tgg tgg gac cag ctg cag gct ggt agc tcg gag       48
Met Gly Ala Pro His Trp Trp Asp Gln Leu Gln Ala Gly Ser Ser Glu
1               5                   10                  15 gtg gac tgg tgc gag gac aac tac acc atc gtg cct gct atc gcc gag       96
Val Asp Trp Cys Glu Asp Asn Tyr Thr Ile Val Pro Ala Ile Ala Glu
            20                  25                  30 ttc tac aac acg atc agc aat gtc tta ttt ttc att tta ccg ccc atc      144
Phe Tyr Asn Thr Ile Ser Asn Val Leu Phe Phe Ile Leu Pro Pro Ile
        35                  40                  45 tgc atg tgc ttg ttt gat gag tat gca aca tgc ttg aac agt gac atc      192
Cys Met Cys Leu Phe Asp Glu Tyr Ala Thr Cys Leu Asn Ser Asp Ile
50                  55                  60 tac tta atc tgg act ctt ttg gtt gta gtg gga att gga tcc gtc tac      240
Tyr Leu Ile Trp Thr Leu Leu Val Val Val Gly Ile Gly Ser Val Tyr
65                  70                  75                  80 ttc cat ttt acc ctt agt ttc ttg ggt cag atg ctt gat gaa ctt gca      288
Phe His Phe Thr Leu Ser Phe Leu Gly Gln Met Leu Asp Glu Leu Ala
                85                  90                  95 gtc ctt tgg gtt ctg atg tgt gct ttg gcc atg tgg ttc ccc aga agg      336
Val Leu Trp Val Leu Met Cys Ala Leu Ala Met Trp Phe Pro Arg Arg
            100                 105                 110 tat cta cca aag atc ttt cgg aat gac agg ggt agg ttc aag gtg gtg      384
```

-continued

```
Tyr Leu Pro Lys Ile Phe Arg Asn Asp Arg Gly Arg Phe Lys Val Val
        115                 120                 125 gtc agt gtc ctg tct gcg gtt acg acg tgc ctg gca ttt gtc aag cct       432
Val Ser Val Leu Ser Ala Val Thr Thr Cys Leu Ala Phe Val Lys Pro
130             135                 140 gcc atc aac aac atc tct ctg atg acc ctg gga gtt cct tgc act gca       480
Ala Ile Asn Asn Ile Ser Leu Met Thr Leu Gly Val Pro Cys Thr Ala
145                 150                 155                 160 ctg ctc atc gca gag cta aag agg tgt gac aac atg cgt gtg ttt aag       528
Leu Leu Ile Ala Glu Leu Lys Arg Cys Asp Asn Met Arg Val Phe Lys
                165                 170                 175 ctg ggc ctc ttc tcg ggc ctc tgg tgg acc ctg gcc ctg ttc tgc tgg       576
Leu Gly Leu Phe Ser Gly Leu Trp Trp Thr Leu Ala Leu Phe Cys Trp
            180                 185                 190 atc agt gac cga gct ttc tgc gag ctg ctg tca tcc ttc aac ttc ccc       624
Ile Ser Asp Arg Ala Phe Cys Glu Leu Leu Ser Ser Phe Asn Phe Pro
        195                 200                 205 tac ctg cac tgc atg tgg cac atc ctc atc tgc ctt gct gcc tac ctg       672
Tyr Leu His Cys Met Trp His Ile Leu Ile Cys Leu Ala Ala Tyr Leu
    210                 215                 220 ggc tgt gta tgc ttt gcc tac ttt gat gct gcc tca gag att cct gag       720
Gly Cys Val Cys Phe Ala Tyr Phe Asp Ala Ala Ser Glu Ile Pro Glu
225                 230                 235                 240 caa ggc cct gtc atc aag ttc tgg ccc aat gag aaa tgg gcc ttc att       768
Gln Gly Pro Val Ile Lys Phe Trp Pro Asn Glu Lys Trp Ala Phe Ile
                245                 250                 255 ggt gtc ccc tat gtg tcc ctc ctg tgt gcc aac aag aaa tca tca gtc       816
Gly Val Pro Tyr Val Ser Leu Leu Cys Ala Asn Lys Lys Ser Ser Val
            260                 265                 270 aag atc acg tga                                                       828
Lys Ile Thr
        275

<210> SEQ ID NO 4
<211> LENGTH: 275
<212> TYPE: PRT
<213> ORGANISM: Homo sapiens

<400> SEQUENCE: 4

Met Gly Ala Pro His Trp Trp Asp Gln Leu Gln Ala Gly Ser Ser Glu
 1               5                  10                  15

Val Asp Trp Cys Glu Asp Asn Tyr Thr Ile Val Pro Ala Ile Ala Glu
                20                  25                  30

Phe Tyr Asn Thr Ile Ser Asn Val Leu Phe Phe Ile Leu Pro Pro Ile
            35                  40                  45

Cys Met Cys Leu Phe Asp Glu Tyr Ala Thr Cys Leu Asn Ser Asp Ile
        50                  55                  60

Tyr Leu Ile Trp Thr Leu Leu Val Val Gly Ile Gly Ser Val Tyr
 65                 70                  75                  80

Phe His Phe Thr Leu Ser Phe Leu Gly Gln Met Leu Asp Glu Leu Ala
                85                  90                  95

Val Leu Trp Val Leu Met Cys Ala Leu Ala Met Trp Phe Pro Arg Arg
            100                 105                 110

Tyr Leu Pro Lys Ile Phe Arg Asn Asp Arg Gly Arg Phe Lys Val Val
        115                 120                 125

Val Ser Val Leu Ser Ala Val Thr Thr Cys Leu Ala Phe Val Lys Pro
    130                 135                 140

Ala Ile Asn Asn Ile Ser Leu Met Thr Leu Gly Val Pro Cys Thr Ala
```

-continued

```
              145                 150                 155                 160
Leu Leu Ile Ala Glu Leu Lys Arg Cys Asp Asn Met Arg Val Phe Lys
                165                 170                 175

Leu Gly Leu Phe Ser Gly Leu Trp Trp Thr Leu Ala Leu Phe Cys Trp
                180                 185                 190

Ile Ser Asp Arg Ala Phe Cys Glu Leu Leu Ser Ser Phe Asn Phe Pro
                195                 200                 205

Tyr Leu His Cys Met Trp His Ile Leu Ile Cys Leu Ala Ala Tyr Leu
                210                 215                 220

Gly Cys Val Cys Phe Ala Tyr Phe Asp Ala Ala Ser Glu Ile Pro Glu
225                 230                 235                 240

Gln Gly Pro Val Ile Lys Phe Trp Pro Asn Glu Lys Trp Ala Phe Ile
                245                 250                 255

Gly Val Pro Tyr Val Ser Leu Leu Cys Ala Asn Lys Lys Ser Ser Val
                260                 265                 270

Lys Ile Thr
            275
```

LIVER TUMOR MARKER SEQUENCES

CROSS-REFERENCE TO RELATED APPLICATIONS

This application claims the benefit of U.S. Provisional Patent Application No. 60/255,674, filed Dec. 14, 2000, which application is incorporated herein by reference as if set forth in its entirety.

STATEMENT REGARDING FEDERALLY SPONSORED RESEARCH OR DEVELOPMENT

This invention was made with U.S. Government Support from the following agency: NIH, Grant No. CA22484. The U.S. Government has certain rights in the invention.

BACKGROUND OF THE INVENTION

Liver cancer is the fifth most common cancer worldwide. More than 400,000 cases were reported in 1990. Hepatocellular carcinoma (HCC) accounts for 80% of all liver cancer. Liver cancer can result from both viral infection and chemical exposure. Known risk factors include hepatitis B and C virus infection and exposure to aflatoxin 1. It is not known whether distinct routes to liver cancer affect the same or different cellular pathways. No mutational model has yet been developed for liver cancer as it has been for other cancers such as colon cancer. The molecular events that precede neoplastic transformation of the liver are not well understood. With no clearly identified cause, successful treatment options are lacking. In fact, the specific genes that are deregulated in liver cancer have not yet been enumerated. This is a critical first step in developing a successful strategy for treating liver cancer.

There is a pressing need to understand the molecular events associated with development of liver cancer, both in humans and in animal model systems where liver cancer is extensively studied, and to provide diagnostic and therapeutic reagents for treating same.

BRIEF SUMMARY OF THE INVENTION

The invention is summarized in that the applicants disclose isolated polypeptides whose expression is deregulated in liver tumor cells from human and non-human animals, relative to the expression in regenerating liver tissue, and further disclose isolated polynucleotides that encode the isolated polypeptides. As a result of this differential expression, the polypeptides and polynucleotides are diagnostic markers for a liver cancer in humans and non-human animals. In humans, the polynucleotides map to a region of chromosome 9p.

In one aspect, the polypeptide is selected from the group consisting of SEQ ID NO:2 and SEQ ID NO:4.

In another aspect, the nucleic acid encodes a polypeptide selected from the group consisting of SEQ ID NO:2 and SEQ ID NO:4.

In yet another aspect, the nucleic acid has a nucleotide sequence selected from the group consisting of an intron-free coding sequence between nucleotides 35 and 859 of SEQ ID NO:1 and all of SEQ ID NO:3. The polynucleotides of SEQ ID NO:1 and SEQ ID NO:3 were obtained from murine and human genetic material, respectively. SEQ ID NO:3 is a predicted spliced cDNA sequence that has been identified in a genomic fragment of the human genome (GenBank Accession No. NT_008335.6, which encompasses sequences previously associated with Accession No. AL391834, named in the above-mentioned provisional patent application). SEQ ID NO:3 is predicted to encode, in humans, a protein within the scope of the invention.

In another aspect, the polypeptide-encoding polynucleotide sequence has at least about 85% nucleotide sequence identity to the coding sequence of SEQ ID NO:1 or SEQ ID NO:3 (using the NCBI Blast 2 comparison protocol) where the polynucleotide hybridizes under stringent hybridization conditions to the polynucleotide of SEQ ID NO:1 or SEQ ID NO:3. Also within the scope of the invention is a nucleic acid having at least about 90%, and most preferably at least 95% identity to either sequence.

In a related aspect, a polynucleotide sequence having greater than 90% homology to the protein-encoding sequences of SEQ ID NO:1 has been identified in a region of human chromosome 9p. A putative protein encoded at that location is greater than 90% similar to the amino acid sequence of SEQ ID NO:2.

In another aspect, the nucleic acid hybridizes under moderately stringent hybridization conditions to a nucleotide sequence selected from the group consisting of SEQ ID NO:1 and SEQ ID NO:3.

In a related aspect, the nucleic acid hybridizes under highly stringent hybridization conditions to a nucleotide sequence selected from the group consisting of SEQ ID NO:1 and SEQ ID NO:3.

In another related aspect, the invention is an oligonucleotide that hybridizes under highly stringent or moderately stringent conditions to a polynucleotide of the invention.

In another aspect, a polynucleotide of the invention, whether from mice or humans or any other source, is engineered into a genetic construct downstream from a heterologous promoter not natively upstream of the polynucleotide that directs expression of the encoded protein. The genetic construct is introduced into a host cell that supports transcription of the polynucleotide and translation of the protein which can then be purified using methods known to those skilled in the art. Alternatively, the construct can be provided in an in vitro transcription/translation system for protein production.

In still another aspect, the invention is an antibody that specifically binds to a polypeptide of the invention.

In yet another aspect, the invention is a method for identifying modulators (inducers or suppressors) of expression of the polynucleotides and polypeptides of the invention, where the method includes the step of observing a change in level of expression of a polynucleotide or polypeptide of the invention in a host cell that expresses the polynucleotide or polypeptide after exposure of the host cell to a modulating agent.

It is an object of the present invention to provide an isolated nucleic acid and an isolated polypeptide that are associated with hepatocellular carcinoma in human and non-human animals.

In yet another aspect, the present invention provides a host cell transfected with the genetic construct described above.

In still another aspect, the invention can relate to a kit having use in a method for determining in a tumor or other cell the expression level of the polypeptide or of a nucleic acid encoding the polypeptide. The kit can contain one or more antibody directed to an epitope on the polypeptide and one or more oligonucleotide or polynucleotide that hybridizes to the nucleic acid that encodes the polypeptide. The kit can also further include additional components for use as positive or negative controls in a method for determining the expression level. Such additional components can include samples of tumor or non-tumor liver cells, or an extract of any of the foregoing, for which a level of expression of a polypeptide or a polynucleotide of the invention has been determined. Alternatively or additionally, the kit can contain a sample of one or more of a polypeptide, a polynucleotide, and an oligonucleotide of the invention for quantification purposes.

Other objects, features and advantages of the present invention will become apparent upon consideration of the following detailed description of the invention.

BRIEF DESCRIPTION OF THE SEVERAL VIEWS OF THE DRAWINGS

Not applicable.

DETAILED DESCRIPTION OF THE INVENTION

Liver cancer is generally studied in animal model systems, preferably in rodent systems, where certain strains have been bred for their high susceptibility to liver tumors. C3H/HeJ mice are highly susceptible to liver tumors after induction with diethylnitrosamine (DEN). To identify polynucleotide sequences or genes that show differential expression in liver tumor cells as compared to normal liver tissue cells, gene expression differences between liver tumors and a regenerating liver were determined using representational difference analysis (RDA: Lisitsyn, et al., *Science* 259:946 (1993), incorporated by reference as if set forth herein in its entirety.

In this application, the applicants report the amino acid sequences of a pair of polypeptides from murine animals and humans (and the sequences of the nucleic acids that encode the polypeptide sequences) that are highly differentially expressed in cells of human and non-human liver tumors relative to regenerating normal liver cells. The polypeptide is conveniently referred to as CRG-L1 although the designation is merely arbitrary. Further, the invention provides materials and methods for detecting expression (and changes in expression) of the nucleic acids (including mRNA, single or double stranded DNA, cDNA and the like) and production of the polypeptides, thereby facilitating use as a diagnostic marker for liver cancer and as a system for assessing putative therapeutic agents.

The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Structurally, the nucleic acid sequence of murine CRG-L1 (SEQ ID NO:1) encodes a polypeptide of about 275 amino acids with a predicted molecular weight of about 30 to 35 kDA. In particular, the murine CRG-L1 includes seven putative transmembrane domains that correspond to amino acids 33–53, 62–82, 91–111, 123–143, 146–166, 174–194, and 212–232 of SEQ ID NO:2.

The nucleic acid sequences of the invention can be introduced conventionally into, and expressed in, host cells which can be prokaryotic (such as bacteria) or eukaryotic (such as yeast, insect, amphibian or mammalian cells) whereupon the transcription of nucleic acid and the properties of the encoded proteins can be assessed.

The isolation of a biologically active polypeptide that is differentially regulated in a liver tumor provides a means for assaying for inhibitors and activators (in vivo or in vitro) of such a polypeptide that can affect the development or progression of liver tumors. For example, the polypeptide can be expressed in cells and the effect of various test agents on mRNA or protein expression level relative to untreated controls can be measured. Alternatively, the level of expression can be assessed in biological samples taken directly from a human or non-human tissue.

The presence and level of such a differentially regulated protein can be readily discerned using antibodies directed to an epitope on the protein using well known methods, such as an ELISA method. The level of gene expression in a liver tumor and in regenerating liver tissue can also be measured using methods for hybridizing nucleic acids (including, without limitation, RNA, DNA, and cDNA). Such methods are generally known to those skilled in the art, but are enabled by the disclosure herein of a liver tumor-specific sequence. Because one can assess levels of expression of protein and nucleic acid, it is also, therefore, possible to develop agonists and antagonists of the encoded protein or to identify agents that affect transcription or translation of the disclosed nucleic acid sequences.

A skilled artisan understands that polypeptide sequences presented herein can vary somewhat, whether as a result, e.g., of sequencing error or allelic variation or duplication, from the sequence presented while still retaining their essential nature, that is, differential regulation in liver tumors relative to normal liver tissue. Further, the nucleic acids of the invention include conservatively modified variants of the sequences presented herein, complementary sequences, and splice variants. In view of the known degeneracy in the genetic code, the proteins disclosed can also be encoded by a large number of other polynucleotide sequences, all of which are within the scope of the invention. The polypeptides of the invention includes polymorphic variants, alleles, mutants, and interspecies homologs that (1) are differentially expressed in liver tumors, (2) bind to antibodies raised against the coding region of either disclosed polypeptide, (3) specifically hybridize under stringent hybridization conditions to a nucleic acid sequence selected from a group consisting of SEQ ID NO:1 and SEQ ID NO:3, or (4) are amplified by primers that amplify SEQ ID NO:1 and SEQ ID NO:3.

Exemplary high stringency hybridization conditions include 50% formamide, 5X SSC and 1% SDS incubated at 42° C., or 5X SSC and 1% SDS incubated at 65° C., followed by washing in 0.2X SSC and 0.1% SDS at 65° C. Exemplary moderate stringency hybridization conditions include 40% formamide, 1M NaCl and 1% SDS incubated at 37° C. followed by washing in 1X SSC at 45° C. These conditions are merely exemplary as one skilled in the art is readily able to discern stringent from moderately stringent hybridization conditions.

Moreover, the sequences of the invention also encompass substitutions, additions and deletions of the sequences presented where the change affects one or a few amino acids in the presented polypeptide sequences, without substantial effect upon the activity of the polypeptide.

The present invention will be better understood upon consideration of the following non-limiting example.

EXAMPLE

Inbred C3H/HeJ mice were bred and housed in plastic cages on corncob bedding (Bed-O'Cobs; Anderson Cob Division) and were fed Breeder Blox (Harlan). Food and acidified water were available ad libitum. To obtain regenerating livers, partial hepatectomies were preformed on male, six week old mice as described by Lukas, E. R., et al., *Molecular Carcinogenesis* 25:295–303 (1999). All papers mentioned in the example are incorporated by reference herein as if set forth in their entirety. Animals were sacrificed 36 hours after the surgery, at a time that corresponds to peak DNA synthesis, and the liver remnants were harvested.

Liver tumors were taken from male C3H/HeJ mice that had been treated with DEN (0.1 µM/g of body weight) at 12 days of age and sacrificed at 32 weeks of age.

Total RNA was extracted from liver using guanidine thiocyanate/CsCl as described by Lukas et al. PolyA mRNA was isolated from 250 µg of total RNA using Oligotex mRNA kit (Qiagen). The cDNA RDA protocol developed by Hubank, M. and D. G. Schatz, *Nucleic Acid Research* 22:5640–5648 (1994) was followed in detail using polyA RNA from the regenerating livers and the liver tumors. cDNA RDA is a method for cloning transcripts found in the pool of mRNA from one source, but absent from the pool of mRNA from a second source. Depending upon how the experiment is set up, one can identify novel genes that are either up-regulated or down-regulated. Briefly, mRNA is obtained from two tissues, in this case regenerating livers and liver tumors. The cDNA RDA technique is performed on cDNA prepared using standard methods from the isolated mRNA.

In the first subtractive round, the representations were hybridized to each other in a 1:100 tester/driver ratio. The second and third difference products used a tester/driver ratio of 1:800 and 1:400,000 respectively. Difference products were subcloned from the second difference product subtractive round because no products were observed in the third round. Cloned products were sequenced by Big Dye Sequencing (Applied Biosystems, Inc.). Two comparisons were performed between the regenerating livers and the liver tumors. In the first comparison, the tester, provided in a more limited amount than the driver, was cDNA derived from the liver tumor. This comparison can identify genes upregulated in liver tumors. In the second comparison, the tester was cDNA derived from the regenerating liver. This comparison can identify genes upregulated in regenerating livers. A number of difference products were obtained in each comparison, indicating that some mRNAs are up-regulated in liver tumors while other mRNAs are down-regulated in liver tumors, relative to regenerating liver tissue. Many of the up-regulated and down-regulated sequences correspond to known genes. In addition, however, five novel differentially expressed transcripts were also identified.

The most highly differentially expressed polynucleotide sequence was examined for expression in eight mouse tissues and in four embryonic tissues using a multiple tissue cDNA panel (Clontech) according to the manufacturer's recommended protocol. The isolated RDA fragment included bases 997 through 1383 of SEQ ID NO:1. The polynucleotide was expressed most highly in heart, lung, and testes. Modest expression was seen in regenerating liver, which is consistent with the low levels observed in the RDA when compared to a liver tumor.

A cDNA clone of the differentially expressed polynucleotide was obtained by screening the Origene rapid-screen mouse liver cDNA library with primers designed from the isolated RDA fragment. A 4.175 kb cDNA was isolated and sequenced. At the 3' end of the cDNA, significant homology to twenty-three mouse ESTs (GenBank Accession Numbers AA048715, AA212916, AA212925, AA462019, AA462654, AA475320, AA914194, AV227941, AW490555, AW701866, AW702104, BB108761, BB627599, BB660847, BB752973, BB764116, BF144307, BF468547, BF661433, BF662488, BG109928, BG230006, and BI080821) was noted. An ATG translation initiation site was seen at base pairs 35–45 of SEQ ID NO:1, with an open reading frame extending to base 862, and followed by a stop codon. The predicted translation product is a protein of 275 amino acids having a molecular weight of 31.4 kD. Seven putative transmembrane domains were revealed using the SMART (Simple Modular Architecture Research Tool) which analyzes protein sequences for motifs. The transmembrane domains correspond to amino acids 33–53, 62–82, 91–111, 123–143, 146–166, 174–194, and 212–232 of SEQ ID NO:2. The existence of related sequences in *C. elegans* and *D. melanogaster* suggest a conserved function for the polynucleotide obtained by the inventors.

In the human genome data base at NCBI, clone Hs9_8492 (Genbank Accession No. NT_008335.6, a contig from human chromosome 9p, was shown to have areas of significant homology to the entire mouse cDNA sequence. In this clone obtained from human DNA, six exons having significant homology to the mouse polynucleotide sequence were identified. The entire sequence in humans of an open reading frame that corresponds to murine SEQ ID NO:1 is represented in clone Hs9_8492.

The human sequences thus identified were joined with reference to the disclosed SEQ ID NO:1 by removing putative splice regions and pasting the remaining sequences together to join as SEQ ID NO:3 the following areas of the contig, in this order: 660483–660351, 645683–645565, 644843–644705, 634599–634459, 623266–623125, and 619093–618907 (as those sequences are numbered as of the filing date of the application in the sequence of Hs9_8492, which contains a set of 21 as yet unlocalized pieces. This single clone includes all of the sequences that, when arranged to form coding sequence 1–825 (plus a stop codon) of SEQ ID NO:3, correspond to a polynucleotide sequence from bases 35 to 862 of SEQ ID NO:1 from mice. Further, such a sequence can encode a protein in humans that corresponds to the protein of SEQ ID NO:2. The putative human cDNA is 87% identical to the mouse sequence. If the putative human cDNA is translated, the resulting amino acid sequence is 91% similar to the corresponding portion of the mouse amino acid sequence, using the Lipman-Pearson protein alignment with a gap penalty of 4 and gap length penalty of 12.

Sequences corresponding to the basal promoter region have also been identified within Hs9_8492 from 661112 to 660393. SPI (660696–660703 and 660616–660622) and E2F (660543–660551) transcription factor binding sites have also been identified upstream of the coding sequence of the human coding sequence. Cotransfections using luciferase reporters have shown that the CRG-L1 promoter is activated by E2F1.

The polynucleotide and polypeptide sequences provide a skilled artisan with the ability to assess using conventional methods the expression levels of this human gene and array of tissues and more specifically to monitor the expression of the gene in human liver tumors as compared to normal human liver tissue. Likewise, antibodies directed to a portion of the human protein can be produced and used as diagnostic agents for assessing protein levels in various human tissues including liver tumors.

The applicants have observed by RT-PCR analysis that, like the murine mRNA, the human CRG-L1 mRNA is upregulated relative to normal liver tissue in three different surgically-excised human hepatocellular carcinomas and one hepatocellular adenoma. The mRNA level in these samples was comparable to that observed in the HepG2 hepatocellular carcinoma cell line. Differential expression of CRG-L1 mRNA was not observed in human colon adenocarcinomas.

The applicants have also observed that other proteins from mouse and human libraries interact with the C-terminal domain in a yeast two-hybrid screen, namely clathrin adapter protein AP-1, megakaryocyte stimulating factor and Jab-1.

The present invention is not intended to be limited to the foregoing, but rather to encompass all such variations and modifications as come within the scope of the appended claims.

We claim:

1. An isolated nucleic acid comprising a coding sequence for a polypeptide selected from the group consisting of SEQ ID NO:2 and SEQ ID NO:4.

2. A genetic construct comprising a polynucleotide of claim 1 downstream from a heterologous promoter.

3. A host cell transfected with the genetic construct of claim 2.

4. A method for identifying modulators of expression of a polynucleotide consisting of a coding sequence for a polypeptide selected from the group consisting of SEQ ID NO:2 and SEQ ID NO:4, the method including the step of observing a change in the level of expression of the polynucleotide in the host cell of claim 3 after exposure of the host cell to a modulating agent.

5. The isolated nucleic acid of claim 1, wherein the coding sequence is selected from the group consisting of the coding sequence of SEQ ID NO:1 and the coding sequence of SEQ ID NO:3.

* * * * *